United States Patent [19]

Shockey et al.

[11] Patent Number: 4,994,033
[45] Date of Patent: Feb. 19, 1991

[54] INTRAVASCULAR DRUG DELIVERY DILATATION CATHETER

[75] Inventors: Rick L. Shockey, Eagan; Robert A. Van Tassel, Excelsior, both of Minn.

[73] Assignee: Schneider (USA) Inc., Minneapolis, Minn.

[21] Appl. No.: 356,520

[22] Filed: May 25, 1989

[51] Int. Cl.$^5$ ............................................. A61M 29/00
[52] U.S. Cl. ...................................... 604/101; 604/96; 606/194
[58] Field of Search .................... 604/52, 53, 96, 101, 604/102, 103, 264, 280; 606/191, 192, 194; 128/207.15

[56] References Cited

U.S. PATENT DOCUMENTS

| | | | |
|---|---|---|---|
| 3,173,418 | 3/1965 | Baran | 128/207.15 |
| 4,338,942 | 7/1982 | Fogarty | 606/194 |
| 4,417,576 | 11/1983 | Baran | 604/101 |
| 4,423,725 | 1/1984 | Baran et al. | 128/207.15 |
| 4,641,653 | 2/1987 | Rockey | 606/194 |
| 4,692,200 | 9/1987 | Powell | 606/192 |
| 4,693,243 | 9/1987 | Buras | 604/96 |
| 4,744,366 | 5/1988 | Jang | 606/194 |
| 4,799,479 | 1/1989 | Spears | 606/194 |

FOREIGN PATENT DOCUMENTS

| | | | |
|---|---|---|---|
| 8912478 | 12/1989 | PCT Int'l Appl. | |
| 1069826 | 1/1984 | U.S.S.R. | 128/207.15 |

Primary Examiner—Stephen C. Pellegrino
Assistant Examiner—Ralph Lewis
Attorney, Agent, or Firm—Haugen and Nikolai

[57] ABSTRACT

An intravascular catheter designed to apply a liquid medicament or other substance to a stenotic lesion as the blood vessel is undergoing dilatation to facilitate the restoration and long-term maintenance of patency to the blood vessel. It comprises three concentrically arranged flexible plastic tubes and a pair of concentrically arranged expander members located at the distal end of the tubes. The space between the outer wall of the inner tube and the inner wall of the intermediate tube is in fluid communication with the interior of the first expander member while the space between the outer wall of the intermediate tube and the inner wall of the outer tube is in fluid communication with the interior of the second expander member. A plurality of minute holes are formed through the second expander member such that when the liquid medicament is introduced into the lumen of the outer tube while an inflation fluid is introduced into the lumen of the intermediate tube, both expander members inflate with the drug or other substance being ejected out through the tiny pores of the outermost expander member while continued inflation of the inner expander member provides the necessary pressure for dilatation of the lesion.

8 Claims, 1 Drawing Sheet

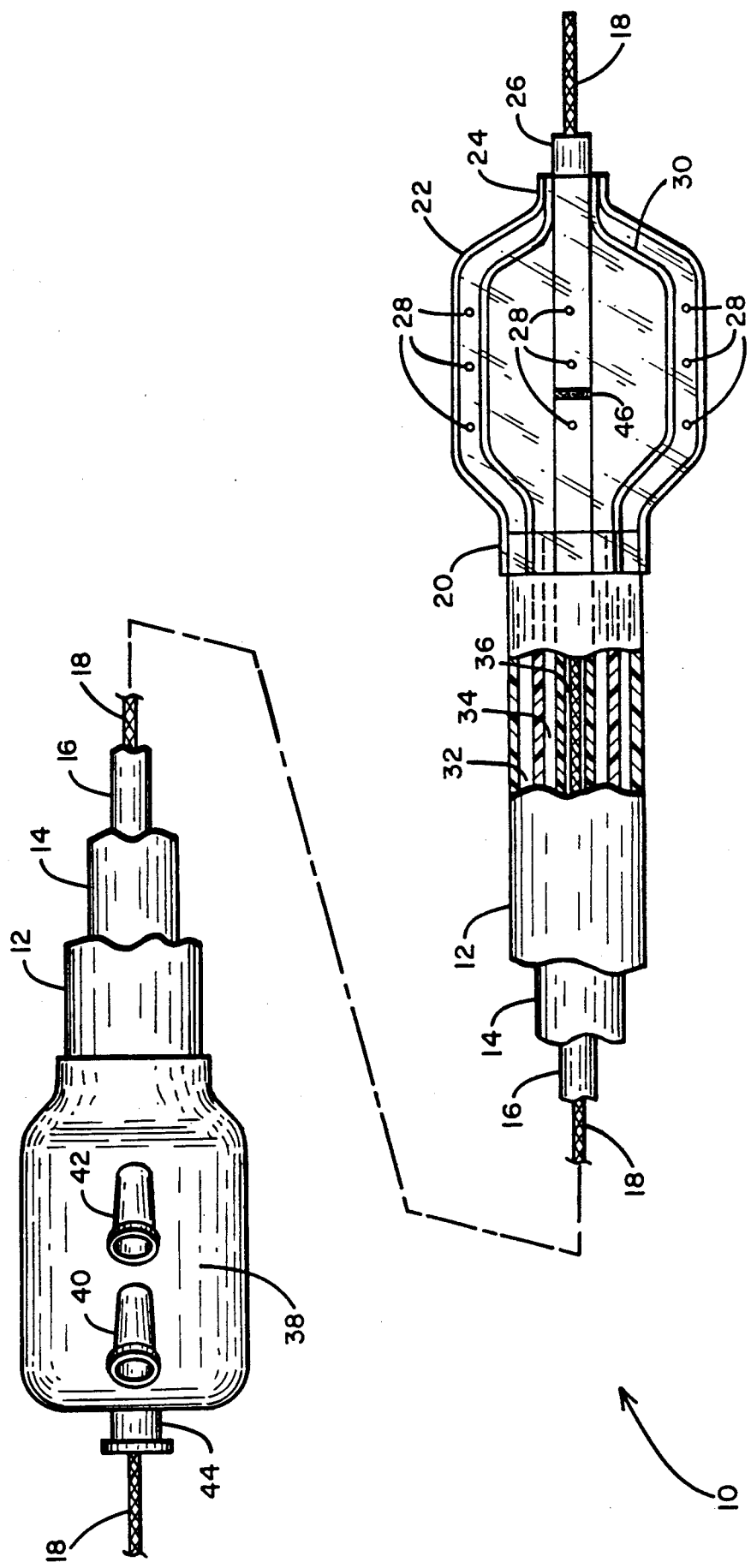

INTRAVASCULAR DRUG DELIVERY DILATATION CATHETER

BACKGROUND OF THE INVENTION

I. Field of the Invention

This invention relates generally to an apparatus and method for performing percutaneous transluminal angioplasty and more particularly to an improved catheter arrangement for allowing simultaneous dilatation of the lesion being treated and the administration of an appropriate drug or other liquid substance at the treatment site.

II. Discussion of the Prior Art

Prior to the mid-1970's, the principal method of treating atheromas or other stenotic lesions in a blood vessel was to surgically excise the blockage or, in the case of coronary arteries, bypass the plugged arteries with a graft usually harvested from the patient's leg. More recently, and following a procedure first advanced by Dr. A. Gruenzig, a balloon catheter is introduced at an appropriate location and routed through the vascular system to the site of the lesion to be treated. With the balloon juxtaposed relative to the blockage or constriction, an inflation fluid is introduced through the lumen of the catheter and made to inflate the balloon to expand same against the blockage and to spread or open the obstructed blood vessel. Such a procedure is far less traumatic than prior surgical procedures.

The patent literature contains an appreciable number of patents pertaining improvements in dilatation catheter structures. Generally speaking, they address improvements in materials employed, torquing characteristics, and, of course, size reduction so that relatively small blood vessels can be treated. A problem still remains with the percutaneous transluminal coronary angioplasty (PTCA) procedure in that the treated blood vessel sometimes does not remain patent. In fact, and perhaps 33 percent of the cases, within 12 months it is necessary to repeat the procedure. It has long been known that certain drugs are effective in reducing the reformation of certain types of stenotic lesions. For example, there are drugs under evaluation which show a tendency to inhibit smooth muscle cell growth. Because of the nature of this drug, it is not desirable that it be injected as a bolus dose and merely be allowed to be carried by the blood stream to the situs of the lesion. This is because in the dosage which would be required, that drug can have undesirable side effects. However, and in accordance with the present invention, if that drug can be administered directly to the lesion, a significantly smaller dosage may be employed and the side effects minimized.

It has also been suggested that following the angioplasty or atherectomy procedure that a mechanical stent be inserted and positioned at the treatment site to inhibit restenosis. However, to date no effective way, other than a direct surgical access, has been devised for positioning the stent. Because in the case of coronary artery repair rather traumatic surgery is required, the advantages of balloon angioplasty are wasted.

OBJECTS

It is accordingly a principal object of the present invention to provide an improved dilatation catheter.

Another object of the invention is to provide a dilatation catheter which permits the administration of a liquid medicament or other substance directly to the lesion being treated to inhibit restenosis.

Another object of the invention is to provide a dilatation catheter in which the stenotic lesion being treated can be spread and expanded at the same time that it is sprayed with a plaque reducing drug or a substance which forms a stent in situ.

A yet further object of the invention is to provide a multi-lumen dilatation catheter having at its distal end a pair of concentric expanders, the outer one being supplied with a drug to be released and the inner one to an inflation fluid for effecting the dilatation and drug administration.

SUMMARY OF THE INVENTION

The intravascular drug delivery dilatation catheter of the present invention comprises three elongated, flexible, plastic tubes which are concentrically disposed relative to one another. Located at the distal end of the concentric tubes are inner and outer hollow expander sleeves. The inner expander sleeve is bonded at its proximal end to the distal end portion of the intermediate tube while the distal end of that inner sleeve is bonded to the distal end of the innermost tube. In a somewhat similar fashion, the outer hollow expander sleeve is bonded at its proximal end to the outermost tube and at its distal end to the distal end of the innermost tube. In this way, the interior of the innermost sleeve is in fluid communication with the lumen of the intermediate tube while the interior of the outermost sleeve is in fluid communication with the lumen of the outermost tube. The outermost sleeve is provided with a pattern of microholes such as formed by a precisely controlled laser beam. A suitable manifold is connected to the proximal ends of the three concentrically disposed catheters for allowing the introduction of an inflation fluid into the lumen of the intermediate tube and an appropriate drug or other substance in liquid form into the lumen of the outer tubular member. In this way, as the pressure is increased within the innermost sleeve causing it to "balloon" out, the drug is simultaneously forced through the micro-apertures to spray and bathe the lesion being treated with the medicament or substance.

DESCRIPTION OF THE DRAWING

The foregoing features, objects and advantages of the invention will become apparent to those skilled in the art from the following detailed description of a preferred embodiment, especially when considered in conjunction with the accompanying drawing in which there is illustrated a greatly enlarged, partially sectioned intravascular drug delivery catheter in accordance with the present invention.

DESCRIPTION OF THE PREFERRED EMBODIMENT

Referring to the drawing, there is indicated generally by numeral 10 the intravascular, drug-delivery dilatation catheter comprising a preferred embodiment of the invention. It is seen to include first, second and third concentrically or coaxially disposed elongated flexible plastic tubular members identified by numerals 12, 14 and 16, respectively. The three tubes may typically be approximately 135 cms. in length with the outermost tube 12 being dimensioned to readily pass through the portion of the vascular system proximal of the treatment site. The arrangement is depicted as an over-the-wire system in that it may be made to pass over an elongated guidewire 18 once that guidewire has been routed through a guide catheter (not shown) with the distal end of the guidewire passing through the site of the lesion and beyond.

Appropriately bonded to the outer surface of the outermost tube 12 at its distal end 20 is a first expander member 22 in the form of a thin membrane sleeve. The distal end 24 of the sleeve 22 is bonded to the exterior surface of the expander member 30 at its distal end. A pattern of micropores as at 28 is formed through the wall of the expander member 22. Where the expander member 22 comprises a biaxially oriented thermosetting plastic material such as polyethylene tetrathalate or polyvinyl chloride, the micropores 28 may be formed using a precision laser.

Located in the interior of the outer expander member or sleeve 22 is an inner expander sleeve 30. It is bonded at its proximal end to the exterior surface of the intermediate tube 14. Its other (distal) end is bonded to the exterior surface of the innermost tube 16. It is readily apparent from the partially sectioned portion of the view that the lumen 32 of the outermost tube 12 is in fluid communication with the interior of the outer expander member 22 while the lumen 34 of the intermediate tube is in fluid communication with the interior of the innermost expander member 30. The lumen 36 of the innermost tube is reserved for the guidewire 18 as illustrated.

Suitably attached to the proximal end of the catheter assembly is a molded plastic hub 38 having a pair of ports 40 and 42, respectively communicating with the lumens 32 and 34. The ports 40 and 42 may be configured with a Luer connection for facilitating the attachment of an inflation tool such as a syringe of the type shown in the Goodin et al U.S. Pat. No. 4,723,938, which is assigned to the assignee of the present invention.

Disposed on the proximal end of the hub 38 is a bore 44 which joins to the lumen 36 of the innermost tube for accommodating the guidewire 18. When the guidewire 18 is removed, the lumen 36 of the innermost tube may be utilized to perfuse blood distally of the treatment site to inhibit ischemia downstream or to introduce a contrast media. Alternatively, the lumen of the innermost tube 16 can be used as a way of measuring pressure at the treatment site or for aspirating any tissue particles which may break loose during the treatment procedure.

The catheter bodies 12, 14 and 16 may be made from a variety of materials now commonly used in fabricating angioplasty and angiographic catheters. Typical materials are PVC, nylon and polyurethane. The guidewire 18 may be fabricated from stainless steel also in accordance with techniques well-known in the patent literature.

In use, the guidewire 18 would conventionally be routed through a guide catheter (not shown) and across the lesion to be treated. Following that, the distal end of the innermost tube 16 is fitted over the proximal end of the guidewire and then advanced along the guidewire until the expander members 22 and 30 are juxtaposed with the lesion to be treated. In the drawing, the expanders 22 and 30 are shown in their inflated configuration, it being understood that during the routing operation, those expanders would tightly conform to the exterior of the tubular member 16.

Once the distal end of the catheter is appropriately positioned with the aid of a radiopaque marker band 46, the selected drug or other material is introduced through the proximal port 40 and through the lumen 32 and into the confines of the outer expander member 22. The injection of the drug will cause some enlargement of the outer expander member 22 but typically the pressure at which the drug material is injected is below the point where substantial amounts of the drug are ejected out through the micropores 28. To perform the simultaneous substance delivery and dilatation, an inflation fluid is next injected through the port 42 and thence through the lumen 34 into the interior of the expander sleeve 30. As the pressure is increased, typically approaching seven to ten atmospheres, the expander member inflates to its predetermined maximum diameter and, in doing so, forces the liquid substance through the ports 28 to effectively spray the lesion being treated with a particular drug or other material. The expansion of the inner sleeve 30 also results in pressure being exerted against the lesion, forcing it against the vessel wall as the drug or other substance is delivered. The combination of the dilatation pressure and the drug substance release will been found to be effective in providing long-term patency to the treated blood vessel.

Those skilled in the art will also recognize that instead of utilizing three concentric tubes as shown in the drawings, a single extruded tube with three parallel lumens may also be utilized to provide inflation and drug delivery.

While purely exemplary, drugs may include aspirin or persantin for inhibiting platelet aggregation at the site, a heprin or prostaglandim for inhibiting clotting or other drugs found to be effective in inhibiting smooth muscle cell growth. It is also contemplated that a light curable biocompatible silicone of the type offered by General Electric Corp., Dow Corning Corp. and others can be injected through the drug delivery catheter of the present invention and then immediately cured with 480 nm visible light, applied via an optical fiber, to form a solid tubular stent in situ.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An intravascular material delivery dilatation catheter comprising:
   first, second and third elongated, flexible, hollow, plastic tubular members of descending diameter concentrically disposed relative to one another and each having a proximal end, a distal end and defining a lumen extending between the proximal end and the distal end, the distal end of the third tubular member extending beyond the distal ends of the first and second tubular members:
   inner hollow expansible sleeve means bonded at one end to the third tubular member near the distal end thereof and at the other end to the distal end of the second tubular member, the interior of the inner hollow expansible sleeve means further being in fluid communication with the portion of the lumen defined by the second tubular member outside the third tubular member;

outer hollow expansible membrane sleeve means bonded at one end near the distal end of the third tubular member and at the other end to the distal end of the first tubular member, the interior of the outer hollow sleeve means further being in fluid communication with the portion of the lumen of the first tubular member defined between the first and second tubular members, the outer hollow sleeve means including a pattern of minute openings extending radially therethrough; and manifold means connected to the proximal ends of the first and second tubular members for introducing an inflation fluid into the lumen of the second tubular member outside the third tubular member and a liquid dispersant into the lumen of the first tubular member outside the second tubular member whereby an amount of dispersant can be caused to perfuse through the minute openings in the outer sleeve means as the inner hollow sleeve means is expanded by the inflation fluid.

2. The drug delivery dilatation catheter of claim 1 further characterized by a guidewire insertable through the lumen defined by the third tubular member.

3. The material delivery dilatation catheter of claim 1 wherein the inner and outer sleeve means comprise biaxially oriented thermoplastic membranes.

4. The material delivery dilatation catheter of claim 3 wherein the membranes comprise a polyethylene terephthalate.

5. A method for treating an atherosclerotic lesion on the interior wall of a blood vessel comprising the steps of:

providing a dilatation catheter comprising first, second and third elongated, flexible, hollow plastic tubular members concentrically disposed relative to one another and each having a proximal end, a distal end defining a lumen extending between the proximal end and the distal end;

inner hollow expander membrane sleeve bonded at one end to the third tubular member near the distal end thereof and at the other end to the distal end of the second tubular member, the interior of the inner hollow expander defined by the sleeve being in fluid communication with the lumen of said second tubular member outside the third tubular member;

outer hollow expander membrane sleeve bonded at one end near the distal end of the third tubular member and at the other end to the distal end of the first tubular member, the interior of the outer hollow expander sleeve being in fluid communication with the lumen defined between the first and second tubular members, the outer hollow expander sleeve including a pattern of minute openings extending radially therethrough; and manifold means connected to the proximal ends of the first and second tubular members for introducing an inflation fluid into the lumen of the second tubular member and a liquid medicament into the lumen of the first tubular member in a manner whereby the medicament can perfuse through the openings in the outer expander sleeve as the inner sleeve expands;

routing the dilatation catheter through the patient's vascular system until the expander sleeves are juxtaposed relative to the lesion;

inflating the inner expander member to apply pressure against said lesion; and simultaneously perfusing a dispersant through the outer expander member and onto the lesion.

6. The method of claim 5 wherein the dispersant is a drug containing liquid.

7. The method of claim 6 wherein the dispersant is a liquid plastic adapted to solidify in situ.

8. The method of claim 5 including the step of introducing a guidewire through the patient's vascular system to the site of the lesion prior to introducing the dilatation catheter.

* * * * *